US008735531B2

(12) United States Patent
Hosokawa et al.

(10) Patent No.: US 8,735,531 B2
(45) Date of Patent: May 27, 2014

(54) DIOL, AND POLYCARBONATE RESIN OR POLYESTER RESIN

(71) Applicant: Canon Kabushiki Kaisha, Tokyo (JP)

(72) Inventors: Katsumoto Hosokawa, Tokyo (JP);
Takahiro Kojima, Tokyo (JP);
Toshikazu Takata, Yokohama (JP);
Kazuko Nakazono, Yokohama (JP);
Yasuhiro Kohsaka, Yokohama (JP);
Yasuhito Koyama, Yokohama (JP);
Toshihide Hasegawa, Yokohama (JP);
Ryota Seto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/799,899

(22) Filed: Mar. 13, 2013

(65) Prior Publication Data

US 2013/0197182 A1  Aug. 1, 2013

Related U.S. Application Data

(62) Division of application No. 13/146,761, filed as application No. PCT/JP2010/054467 on Mar. 10, 2010.

(30) Foreign Application Priority Data

Mar. 12, 2009 (JP) .................................. 2009-060271
Mar. 12, 2009 (JP) .................................. 2009-060272

(51) Int. Cl.
*C08G 64/00* (2006.01)

(52) U.S. Cl.
USPC ............ 528/196; 528/125; 528/226; 528/370

(58) Field of Classification Search
USPC ................................... 528/125, 226, 196, 370
See application file for complete search history.

(56) References Cited

U.S. PATENT DOCUMENTS

| 3,546,165 A | 12/1970 | Morgan |
| 5,391,693 A | 2/1995 | Nakae |
| 2008/0085955 A1 | 4/2008 | Yanagida et al. |
| 2013/0165573 A1* | 6/2013 | Kojima et al. ................ 524/413 |
| 2013/0184391 A1 | 7/2013 | Kojima et al. |

FOREIGN PATENT DOCUMENTS

| JP | H04-214718 A | * | 8/1992 |
| JP | 6-234848 A | | 8/1994 |
| JP | H06-234848 A | * | 8/1994 |
| JP | 07-109342 A | | 4/1995 |
| JP | 9-316190 A | | 12/1997 |
| JP | 10-101787 A | | 4/1998 |
| JP | 3294930 B | | 6/2002 |
| JP | 2006-089585 A | | 4/2006 |
| JP | 2008-063296 A | | 3/2008 |
| JP | 4196326 B | | 12/2008 |

OTHER PUBLICATIONS

Ohno, M., et al., "Synthesis of a novel naphthalene-based poly(arylene ether-ketone) by polycondensation of 1,5-bis94-fluorobenzoyl)-2,6-dimethylnaphthalene with bisphenol A," J. Polym. Sci. A, 1995, 2647-2655.*
Ohno, M., et al. "Synthesis and properties of poly(arylene-ether-ketone)s containing a dimethylnaphthalene skeleton in the main chain," Reactive & Functional Polymers, 1996, 30, 149-156.*
Derwent Abstract for Foreign Patent Document JP-H04-214718. Accessed Aug. 22, 2013.*
Translation of JP-H06-234848 performed on JPO website on Aug. 23, 2013.*
Office Action in Chinese Application No. 201080010561.X (dated Jul. 3, 2013).
Machine translation of JP 2006-089585, performed on JPO Website on Mar. 30, 2013.
International Search Report in PCT/JP2010/054467 (dated Dec. 13, 2010).
International Preliminary Report on Patentability in PCT/JP2010/054467 (dated Sep. 22, 2011).

Vladimir Prelog et al., "Chirale 2,2'-polyoxaalkano-9,9'-spirobifluorenes," 62(7) Helv. Chim. Acta 2285-2302 (Oct. 1979).
Non-final Office Action in U.S. Appl. No. 13/146,761 (dated Apr. 9, 2013).
Non-final Office Action in U.S. Appl. No. 13/146,761 (dated Jul. 30, 2013).

\* cited by examiner

*Primary Examiner* — Melissa Rioja
*Assistant Examiner* — Nicholas Hill
(74) *Attorney, Agent, or Firm* — Fitzpatrick, Cella, Harper & Scinto

(57) ABSTRACT

A diol from which a resin material having high processability and a high refractive index can be manufactured, a polycarbonate resin and a polyester resin which is a polymer of the diol, and a molded article and an optical element formed of the polymer. The diol is represented by the general formula (1) shown below; the polycarbonate resin and the polyester resin are polymers thereof; and the molded article and the optical element are formed of the polymers,

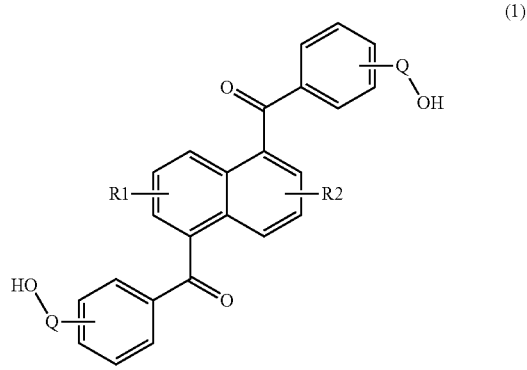

wherein R1 and R2 each independently denote one of a hydrogen atom and an alkyl group having 1 or more and 6 or less carbon atoms; Q denotes one of an oxyethylene group, a thioethylene group and a single bond.

8 Claims, 1 Drawing Sheet

DIOL, AND POLYCARBONATE RESIN OR POLYESTER RESIN

CROSS-REFERENCE TO RELATED APPLICATIONS

This application is a divisional of U.S. application Ser. No. 13/146,761, which was the National Stage of International Application No. PCT/JP2010/054467, filed Mar. 10, 2010, which claims the benefit of Japanese Patent Application No. 2009-060271, filed Mar. 12, 2009, and Japanese Patent Application No. 2009-060272, filed Mar. 12, 2009. All prior applications are hereby incorporated by reference herein in their entirety.

TECHNICAL FIELD

The present invention relates to a novel diol having one of a naphthalene structure and a fluorene structure, and a polymer formed from the diol, particularly, a polycarbonate resin, a polyester resin, and further, a molded article and an optical element formed of the polymer.

BACKGROUND ART

Since resin materials having a high refractive index have higher processability than conventional glass materials, extensive studies are made to apply them to various applications such as eyeglass lenses, lenses for cameras and the like, lenses for optical disks, fθ lenses, optical elements of image display media, optical films, films, substrates, various types of optical filters, prisms, optical elements for communication, and the like.

In particular, resin materials having a fluorene structure are known to have a relatively high refractive index and a relatively low birefringence, and can also be expected to exhibit a high heat resistance, so such resin materials are variously being studied. Japanese Patent No. 4196326 discloses a low-birefringence polycarbonate resin having a 9,9'-diphenylfluorene structure and excelling in heat resistance and mechanical strength.

On the other hand, it is broadly known that naphthalene structures can make resin materials to have a higher refractive index than fluorene structures, and there is stated that a polyvinylnaphthalene has a refractive index of the d line of about 1.68, and is one of the polymers having a high refractive index among common polymers. A naphthalene skeleton has a high symmetry having its planar structure and a long conjugated system. Hence, introduction of a naphthalene structure into a polymer can also be expected to improve mechanical properties of a polymer.

From these backgrounds, resin materials having a naphthalene structure incorporated are variously being studied. For example, Japanese Patent Application Laid-Open No. H09-316190 discloses a novel aromatic diamine to become a raw material for an aromatic polyamide resin and a polyimide resin having a dimethylnaphthalene skeleton and excelling in mechanical strength, heat resistance and processability.

There is a spirobifluorene as a molecule having a structure by which a higher refractive index and a lower birefringence can be expected because of having a higher number of conjugated aromatic rings in a molecule thereof and a higher symmetry of the molecular structure than the conventional 9,9'-diphenylfluorene structure. Japanese Patent Application Laid-Open No. 2006-089585 discloses a resin having a heterocyclic structure having such a spiro carbon as a unit skeleton.

Optical elements are designed utilizing such resins.

DISCLOSURE OF THE INVENTION

However, a polycarbonate resin described in Japanese Patent No. 4196326 includes a resin obtained by homopolymerization of a monomer having a 9,9'-diphenylfluorene structure, or a resin containing a structural unit exhibiting a lower refractive index than such resin. Therefore, in order to achieve a further higher refractive index, a copolymerization component exhibiting a higher refractive index needs to be developed.

If an aromatic diamine compound having a dimethylnaphthalene skeleton described in Japanese Patent Application Laid-Open No. H09-316190 is used, it is difficult to practically sufficiently easily manufacture a polycarbonate resin useful as an optical resin. In order to practically sufficiently easily manufacture a polycarbonate resin and a polyester resin having a naphthalene structure, a diol having a naphthalene structure is needed.

A resin having a heterocyclic structure having a spiro carbon described in Japanese Patent Application Laid-Open No. 2006-089585 can be expected to exhibit a higher refractive index, but there are problems on heat processing, such as a high glass transition point of 334° C. to 340° C., and high costs and easy occurrence of coloration on processing.

It is an object of the present invention, in consideration of the above-mentioned problems, to provide a diol from which resin materials having a high refractive index and high processability can be manufactured, a polymer formed from the diol, particularly, a polycarbonate resin, a polyester resin, and a molded article and an optical element formed of the polymer.

The present invention is to provide a diol of the following <1> to <12>, a polycarbonate resin and a polyester resin formed from the diol, and further, a molded article and optical element formed of the resin.

<1> A diol represented by the following general formula (1):

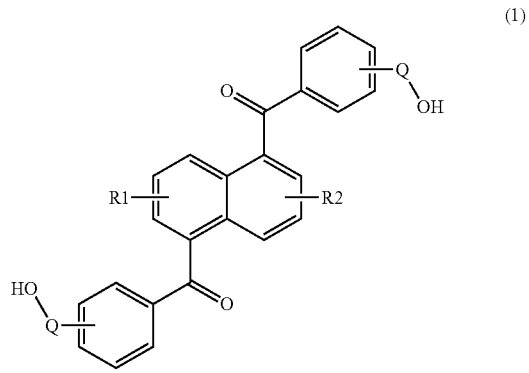

wherein R1 and R2 each independently denote one of a hydrogen atom and an alkyl group having 1 or more and 6 or less carbon atoms; Q denotes one of an oxyethylene group, a thioethylene group and a single bond.

<2> A polycarbonate resin containing in the polymer a repeating unit represented by the following general formula (2):

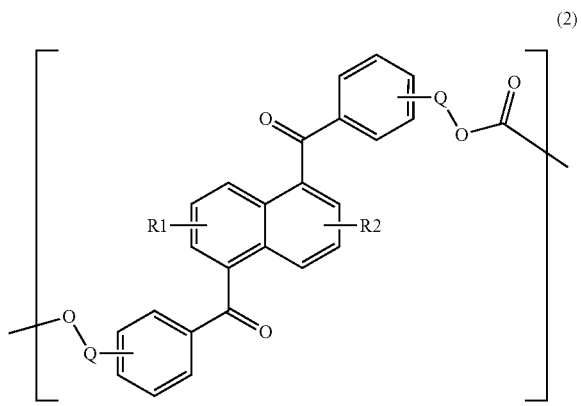

(2)

wherein R1 and R2 each independently denotes one of a hydrogen atom and an alkyl group having 1 or more and 6 or less carbon atoms; and Q denotes one of an oxyethylene group, a thioethylene group and a single bond.
<3> The polycarbonate resin described in <2>, wherein the molar fraction of a repeating unit represented by the general formula (2) is 10% or more (where, the molar fraction is a value, expressed as percentage, obtained by dividing the number of a repeating unit represented by the general formula (2) by the sum of the numbers of all repeating units in the polymer).
<4> A diol represented by the following general formula (3):

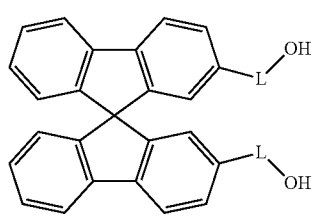

(3)

wherein L denotes one of an oxyalkylene group having 2 or more and 12 or less carbon atoms and a poly(oxyethylene) group having 2 or more and 12 or less carbon atoms.
<5> A polycarbonate resin containing in the polymer a repeating unit represented by the following general formula (4):

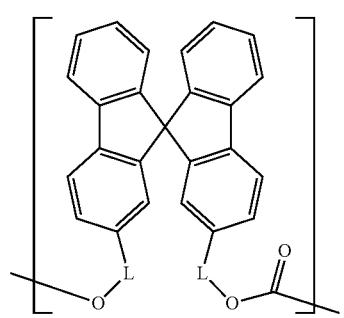

(4)

wherein L denotes one of an oxyalkylene group having 2 or more and 12 or less carbon atoms and a poly(oxyethylene) group having 2 or more and 12 or less carbon atoms.

<6> The polycarbonate resin according to <5>, wherein the molar fraction of a repeating unit represented by the general formula (4) is 10% or more (where, the molar fraction is a value, expressed as percentage, obtained by dividing the number of a repeating unit represented by the general formula (4) by the sum of the numbers of all repeating units in the polymer).
<7> The polycarbonate resin according to <3> or <6>, further containing a repeating unit represented by the general formula (5):

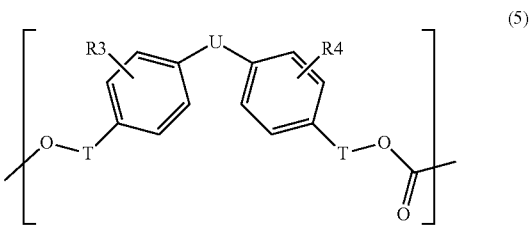

(5)

wherein T denotes one of an oxyalkylene group having 2 or more and 12 or less carbon atoms, a poly(oxyethylene) group having 2 or more and 12 or less carbon atoms, and a single bond; R3 and R4 each denote one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.
<8> A polycarbonate resin containing a repeating unit represented by the general formula (2) shown above and a repeating unit represented by the general formula (6) shown below, further containing a repeating unit represented by the general formula (5) shown above:

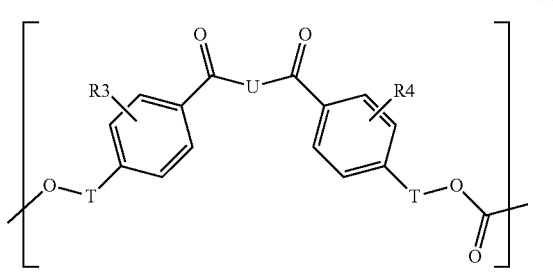

(6)

wherein T denotes one of an oxyalkylene group having 2 or more and 12 or less carbon atoms, a poly(oxyethylene) group having 2 or more and 12 or less carbon atoms, and a single bond; R3 and R4 each denote one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.

<9> A polyester resin containing in the polymer a repeating unit represented by the general formula (7):

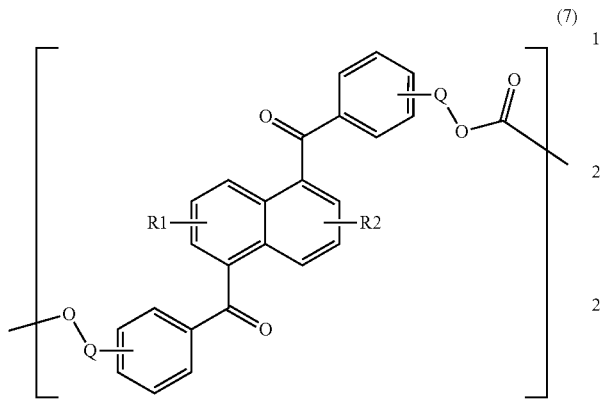

(7)

wherein R1 and R2 each independently denotes one of a hydrogen atom and an alkyl group having 1 or more and 6 or less carbon atoms; and Q denotes one of an oxyethylene group, a thioethylene group and a single bond.

<10> A polyester resin containing in the polymer a repeating unit represented by the general formula (8):

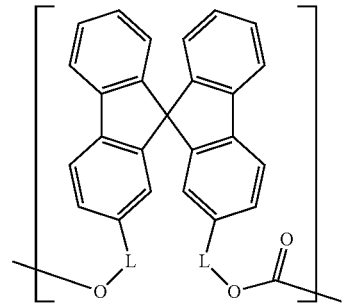

(8)

wherein L denotes one of an oxyalkylene group having 2 or more and 12 or less carbon atoms and a poly(oxyethylene) group having 2 or more and 12 or less carbon atoms.

<11> A molded article including one of a polycarbonate resin and a polyester resin according to any one of <2>, <3> and <5> to <9>.

<12> An optical element including one of a polycarbonate resin and a polyester resin according to any one of <2>, <3> and <5> to <9>.

The present invention can provide a diol from which resin materials having a high refractive index and high processability can be manufactured, a polymer formed from the diol, particularly, a polycarbonate resin, a polyester resin, and a molded article and optical element formed of the resin.

The above and other objects of the invention will become more apparent from the following drawings taken in conjunction with the accompanying drawings.

BRIEF DESCRIPTION OF THE DRAWINGS

FIG. 1 is a graph illustrating relationships between the composition ratio and the optical characteristics of copolymers of monomers 1a and 7a.

BEST MODES FOR CARRYING OUT THE INVENTION

Figure 1:
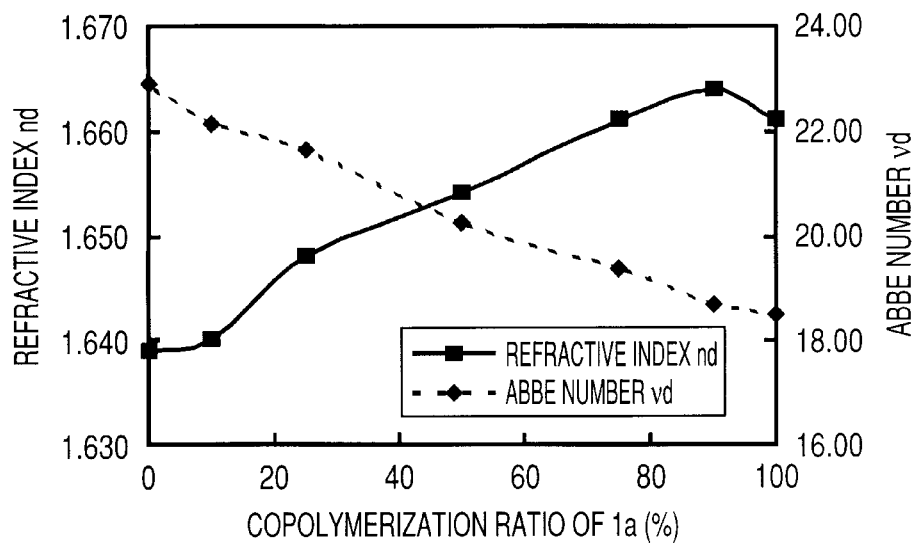

The present invention can achieve the object of the present invention through the above-mentioned constitution; more specifically, the present invention can achieve the object through the following embodiments.

First Embodiment

A diol according to a first embodiment of the present invention is characterized by a compound represented by the following general formula (1):

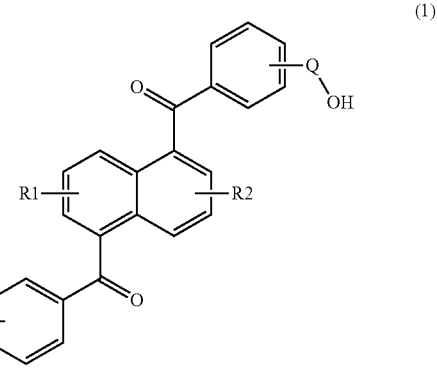

(1)

In the general formula (1), R1 and R2 each independently denote one of a hydrogen atom and an alkyl group having 1 or more and 6 or less, preferably 1 or more and 2 or less, carbon atoms; Q denotes one of an oxyethylene group, a thioethylene group and a single bond. In the general formula (1), the substitution positions of R1 and R2 are preferably 2, 3, 4-positions and 6, 7, 8-positions of the naphthalene ring, and more preferably the 2-position and the 6-position. In the case where the substitution positions of R1 and R2 are the 2-position and the 6-position, in the undermentioned method for manufacturing a diol represented by the general formula (1), since a single structural isomer is obtained, it is advantageous because of unnecessary separation of isomers.

Then, a method for manufacturing a diol according to the present invention is described below.

In a method for manufacturing a diol represented by the general formula (1) according to the present invention, a di-halogeno-compound to be a precursor thereof is first described. A synthesis method of a di-halogeno compound is described, for example, in Japanese Patent No. 3294930. Specifically, a naphthalene compound represented by the general formula (9):

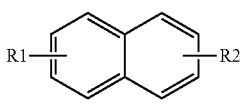

(9)

wherein R1 and R2 each independently denote one of a hydrogen atom and an alkyl group having 1 to 6 carbon atoms, and a benzoyl halide compound represented by the general formula (10):

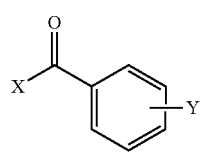

(10)

wherein X and Y each independently denote one of fluorine, chlorine, bromine and iodine atoms,
are allowed to react in the presence of a Lewis acid catalyst, to manufacture a di-halogeno compound represented by the general formula (11):

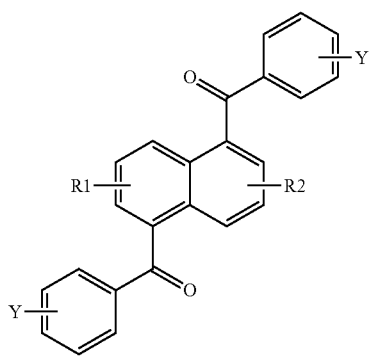

(11)

wherein Y denotes one of fluorine, chlorine, bromine and iodine atoms.

The reaction of a naphthalene compound of the general formula (9) with a benzoyl halide compound of the general formula (10) is the so-called Friedel-Crafts acylation reaction; and a Lewis acid catalyst usable is a strong Lewis acid such as aluminum chloride, iron (III) chloride and boron fluoride.

In this case, the stoichiometric ratio of a naphthalene compound of general formula (9) and a benzoyl halide compound of general formula (10) is such that (naphthalene compound of the general formula (9)(mol))/(benzoyl halide compound of general formula (10)(mol)) is preferably 2 or more and 10 or less, and more preferably 2 or more and 6 or less. When this value is less than 2, there is a risk that by-products are produced and the yield of a di-halogeno compound represented by the general formula (11) decreases; and when the value is more than 10, there is a risk that the use amount of the benzoyl halide compound represented by the general formula (5) becomes much and the cost becomes high in production. The use amount of a Lewis acid is not especially limited, but is generally 2 or more equivalent weights and 4 or less equivalent weights with respect to a naphthalene compound of the general formula (4).

In the case of using a reaction solvent, an organic solvent can be used such as nitromethane, nitrobenzene, chlorobenzene, bromobenzene, and chlorinated hydrocarbons including dichloromethane (methylene chloride), chloroform, dichloroethane, trichloroethane, tetrachloroethane, pentachloroethane and chlorobenzene.

The reaction condition is not especially limited; but generally, the reaction temperature is 10° C. to 50° C., and the reaction needs 12 to 48 hours. A desired di-halogeno-compound represented by the general formula (11) can easily be refined by a method such as recrystallization and chromatography, but can more suitably be refined by a recrystallization method.

Then, the di-halogeno-compound represented by the general formula (11) is converted to a diol represented by the general formula (1) shown before. The conversion can be achieved by reaction with various agents according to the structure of Q in the general formula (1). For example, the compound having a single bond as Q can be directly synthesized by allowing a base such as potassium hydroxide to act, and alternatively may be synthesized by allowing cesium acetate or the like to react for the acetoxylation reaction and thereafter allowing a base to act for the hydrolysis reaction. In this case, since the reaction temperature is preferably 150° C. to 200° C., a high-boiling point polar solvent such as N,N-dimethylformamide and dimethyl sulfoxide is preferably used. The reaction time needs about 12 to 48 hours.

For a diol in which the structure of Q in the general formula (1) is one of an oxyethylene group and a thioethylene group, there are available two synthesis methods. A first method is one in which one of ethylene glycol, 2-mercaptoethanol and the like is allowed to act on a di-halogeno-compound represented by the general formula (11) in the presence of a strong base such as potassium hydroxide and potassium-tert-butoxide. A second method is one in which 2-chloroethanol is allowed to act on a diol having a single bond as the structure of Q in the general formula (1) in an organic solvent such as N,N-dimethylformamide and dimethyl sulfoxide in the presence of cesium carbonate or the like.

The stoichiometric ratio of an alcohol or a thiol allowed to act on a di-halogeno-compound represented by the general formula (11) is such that (alcohol or thiol allowed to act (mol))/(di-halogeno-compound of the general formula (11) (mol)) is preferably 2 or more and 100 or less, and in the case where 2-mercaptoethanol, which has a high nucleophilicity in the presence of a strong base, more preferably two-fold equimolar. When this value is less than 2, there is a risk that by-products are produced and the yield of the diol represented by the general formula (1) decreases; and when the value is more than 100, there is a risk that the use amount of the one of the alcohol and the thiol becomes much and the cost becomes high in production.

In the case where 2-chloroethanol is allowed to act on a diol having a single bond as the structure of Q in the general formula (1), the stoichiometric ratio is such that (2-chloroethanol allowed to act (mol))/(diol of the general formula (1) (mol)) is preferably 2 or more and 100 or less. When this value is less than 2, there is a risk that by-products are produced and the yield of the diol represented by the general formula (1) decreases; and when the value is more than 100, there is a risk that the use amount of 2-chloroethanol becomes much and the cost becomes high in production.

The temperature and the time necessary for the reaction completion differ depending on the kind and the stoichiometric amount of the alcohol and the thiol allowed to react, but in order to avoid the production of by-products, the reaction is preferably carried out generally at a temperature of 150° C. or lower and for 12 to 48 hours. An obtained reaction product can easily be refined by a method such as recrystallization and chromatography, but is more suitably refined by recrystallization.

A diol represented by the general formula (1) according to the present invention has a structure in which a plurality of aromatic rings in one molecule is linked through carbonyl groups. Generally, polymeric materials having a high refractive index are likely to be relatively inferior in processability, in other words, are likely to be relatively high in processing temperature during melt processing, possibly causing an increase in processing costs and the yellowing of the resin. However, since a polymer obtained by polymerization of a diol represented by the general formula (1) according to the present invention conceivably has such an effect that the residue originated from the diol enhance the bendability of polymer main chains, the polymer can be expected to have a high processability in spite of having a relatively high refractive index.

The polycarbonate resin and the polyester resin according to the present invention are characterized by a polymer synthesized from a monomer containing a diol represented by the general formula (1) as a polymerization component to include in the polymer a repeating unit represented by the following general formula (2):

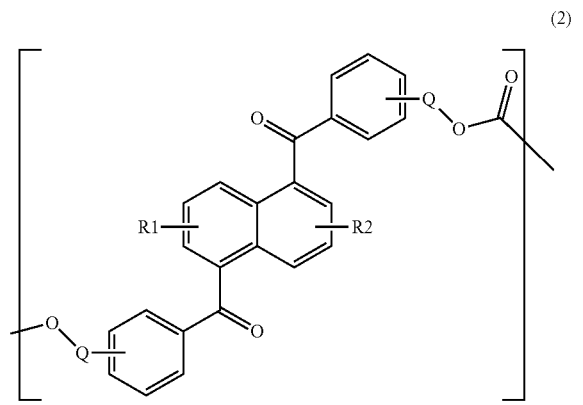

wherein R1 and R2 each independently denote one of a hydrogen atom and an alkyl group having 1 or more and 6 or less carbon atoms; Q denotes one of an oxyethylene group, a thioethylene group and a single bond.

Here, the molar fraction of the repeating unit represented by the general formula (2) contained in the above-mentioned polymer is preferably 10% or more, and more preferably 25% or more. Here, the molar fraction is a percentage value obtained by dividing the number of a repeating unit represented by the general formula (2) by the sum of the numbers of all repeating units in the polymer. A larger molar fraction of a repeating unit represented by the general formula (2) results in the condition that the high refractive index of a diol analog of the general formula (1) is strongly reflected on the polymer.

Other copolymerization components in the polymer are not especially limited as long as satisfying desired characteristics, but more suitably contained is a copolymerization component represented by the following general formula (12):

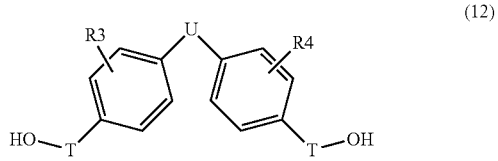

wherein T denotes one of an oxyalkylene group having 2 or more and 12 or less carbon atoms, a poly(oxyethylene) group having 2 or more and 12 or less carbon atoms, and a single bond; R3 and R4 each denote one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.

In the case of using a diol represented by the general formula (12) as a copolymerization component, a synthesized polymer contains a repeating unit represented by the following general formula (5)

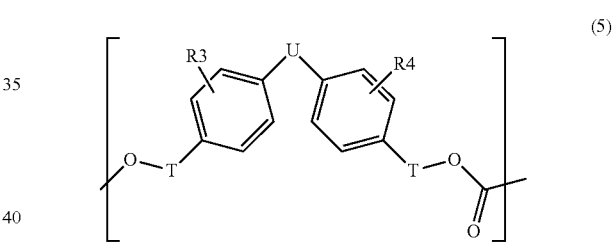

wherein T denotes one of an oxyalkylene group having 2 or more and 12 or less carbon atoms, a poly(oxyethylene) group having 2 or more and 12 or less carbon atoms, and a single bond; R3 and R4 each denote one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.

In this case, the thermal stability and the optical characteristics of a diol analog of the general formula (13) are reflected on the polymer depending on the copolymerization ratio.

A polymer of a diol represented by the general formula (12) may be used as a copolymerization component, and for example, the polymer may have a structure in which oxyalkylene groups or poly(oxyethylene) groups represented by T in the general formula (12) in a plurality of molecules are linked through one of —O—, —S—, —SO$_2$—, —CO— and a single bond. These copolymerization components may be used singly or plurally.

In the case where the polycarbonate resin and the polyester resin according to the present invention contain a repeating unit of the general formula (5), the molar fraction of a repeating unit represented by the general formula (5) is preferably 90% or less, and more preferably 75% or less.

In the case where the polycarbonate resin and the polyester resin according to the present invention contain an optional repeating unit other than those of the formula (2) and the general formula (5), the molar fraction of the repeating unit other than those of the general formulae (2) and (5) is preferably 10% or less. Here, the molar fraction of a repeating unit refers to a percentage value obtained by dividing the total number of the repeating unit other than those of the general formulae (2) and (5) by the sum of the numbers of all the repeating units. If the molar fraction of the repeating unit other than those of the general formulae (2) and (5) exceeds 10%, there is a risk that desired physical properties such as thermal stability, high refractive index and low birefringence cannot be provided.

The polycarbonate resin and the polyester resin according to the present invention can be manufactured by various methods, but can be manufactured using independently one of three methods described below, or can efficiently be manufactured by combining the methods to conduct stepwise polymerization.

A first method involves an interfacial polycondensation in which a diol represented by the general formulae (1) and (12) and phosgene or its derivative are allowed to react in a mixed solution of an organic solvent and a basic aqueous solution.

In this reaction, phosgene or its derivative is introduced in a mixed solution of a basic aqueous solution in which an alkali metal compound and the like are dissolved, a diol represented by the general formulae (1) and (12), and an inactive organic solvent and allowed to react to produce a desired polycarbonate. Here, inactive organic solvents include chlorinated hydrocarbons such as dichloromethane (methylene chloride), dichloroethane, trichloroethane, tetrachloroehtane and chlorobenzene, and actopheneone. The reaction condition is not especially limited, but usually involves cooling in the range of 0° C. to ordinary temperature in the reaction initial period, and thereafter conducting the reaction in the temperatures range of 0° C. to 70° C. for 30 min to 6 hours.

The amount of phosgene or its derivative allowed to act on a diol represented by the general formulae (1) and (12) is preferably such that (phosgene or its derivative allowed to act (mol))/(total of diols used in the reaction (mol)) is 0.3 or more and 1.5 or less. When this value is less than 0.3, there is a risk that an unreacted diol remain and the yield decreases; and when the value is more than 1.5, there is a risk that since the amount of phosgene or its derivative used becomes much, the separation and refinement after the reaction is difficult.

In order to promote the reaction, a phase-transfer catalyst may be added to an organic solvent. Here, phase-transfer catalysts include organic salts such as triethylamine, tetramethylethylenediamine and pyridine.

In order to regulate the polymerization degree, a terminator may be added to the reaction solution. Terminators usable may be ones usually used in polymerization of polycarbonates, and may be various types thereof. The terminators specifically include monohydric phenols such as phenol, p-cresol, p-tert-butylphenol, p-tert-octylphenol, bromophenol and tribromophenol. Phosgene derivatives include bis(trichloromethyl) carbonate, bromophosgene, bis(2,4,6-trichlorophenyl) carbonate, bis(2,4-dichlorophenyl) carbonate, bis(cyanophenyl) carbonate and trichloromethyl chloroformate.

Next, a second method for synthesizing the resin according to the present invention involves the transesterification of a diol represented by the general formulae (1) and (12) and a carbonic diester. There are various types of carbonic diesters used in this method, and suitably used are diphenyl carbonate, ditolyl carbonate, bis(chlorophenyl)carbonate, bis(nitrophenyl)carbonate, dinaphthyl carbonate, bisphenol A bisphenyl carbonate, dimethyl carbonate, diethyl carbonate, dibutyl carbonate, dicyclohexyl carbonate, ethyl phenyl carbonate, butyl phenyl carbonate, cyclohexyl phenyl carbonate and bisphenol A methylphenyl carbonate. In the transesterification, any of diols represented by the general formulae (1) and (12) may be used as a derivative of a carbonic diester.

The amount of a carbonic diester used is preferably such that (carbonic diester allowed to act (mol))/(total of diols used in the reaction (mol)) is in the range of 1.0 or more and 2.5 or less. When this value is less than 1.0, there is a risk that an unreacted diol remain and the yield decreases; and when the value is more than 2.5, there is a risk that since the amount of a carbonic diester used becomes much, the separation and refinement after the reaction is difficult. Also in this transesterification, a terminator cited in the first method may be added as required.

The transesterification can be carried out under the condition of usually 350° C. or lower, and is desirably carried out by gradually raising the temperature after the progress of the reaction under the condition of more preferably 300° C. or lower. The transesterification exceeding 350° C. causes the thermal decomposition of the polymer, which is not preferable. The reaction pressure can suitably be regulated so as to efficiently carry out the reaction depending on the vapor pressure of a monomer used and the boiling point of a product produced by the reaction. In the case where, as a result of the transesterification, by-products other than a polymer produced from an ester compound used can be removed by reduced pressure, in order to improve the reaction rate and the yield, the reaction is preferably carried out by simultaneously removing the by-products under a reduced pressure condition with the progress of the reaction. The reaction needs to be carried out for the reaction time until a target molecular weight is reached, and the reaction time is usually about 10 min to 12 hours.

The transesterification can be carried out batchwise or continuously. The material and the structure of a reactor used are not especially limited, and the reactor suffices if having usual heating function and stirring function. The shape of the reactor may be not only of a tank type, but of an extruder type.

The transesterification is usually carried out under a non-solvent condition, but in the case where the melting point of a diol used is high and the reaction hardly progresses, may be carried out in the presence of 1 to 200% by weight of an inactive organic solvent with respect to a polymer obtained. Here, inactive organic solvents include aromatic compounds such as diphenyl ether, halogenated diphenyl ether, benzophenone, diphenyl sulfone, polyphenyl ether, dichlorobenzene and methylnaphthalene, cycloalkanes such as tricyclo(5.2.10)decane, cyclooctane and cyclodecane, and chlorinated hydrocarbons such as dichloromethane (methylene chloride), chloroform, dichloroethane, trichloroethane, tetrachloroethane, pentachloroethane and chlorobenzene. Further, the transesterification may be carried out under an inactive gas atmosphere as required. Here, inactive gases include, for example, helium, argon, carbon dioxide and nitrogen.

Further, a catalyst usually used can be used in the transesterification, as required. Here, transesterification catalysts usable include, for example, alkali metal compounds and alkaline earth metal compounds such as lithium hydroxide, sodium hydroxide and potassium hydroxide, nitrogen-containing basic compounds such as amines and quaternary ammonium salts, and boron compounds. Above all, nitrogen-containing basic compounds are preferable in view of a high catalytic activity power and the ease of removal from a reaction system, and suitably used are trihexylamine, tetramethylammonium hydroxide, tetrabutylammonium hydroxide, dimethylaminopyridine, and the like.

The use amount of the catalyst is $1\times10^{-2}$ to $1\times10^{-8}$ mol, and preferably $1\times10^{-3}$ to $1\times10^{-7}$ mol, with respect to 1 mol of all diols. The addition amount of the catalyst of less than $1\times10^{-8}$ mol has a risk of not providing a sufficient catalytic effect, and that exceeding $1\times10^{-2}$ mol has a risk of inviting decreases in physical properties of a polymer obtained, especially heat resistance and hydrolysis resistance.

Further, a third method for synthesizing the resin according to the present invention involves allowing a diol represented by the general formulae (1) and (12) to react with a dicarboxylic acid derivative for ester polymerization. Dicarboxylic acid derivatives used in this method are not especially limited, and include aliphatic carboxylic acids such as succinic acid, glutaric acid, adipic acid, pimelic acid, suberic acid and cyclohexanedicarboxylic acid, aromatic carboxylic acids such as phthalic acid, isophthalic acid, terephthalic acid and naphthalenedicarboxylic acid, acid chlorides of these dicarboxylic acids, methyl esters of these dicarboxylic acids, ethyl esters of these dicarboxylic acids, and dicarboxylic anhydrides such as phthalic anhydride and naphthalenedicarboxylic anhydride.

The amount of a dicarboxylic acid derivative used is preferably such that (dicarboxylic acid derivative allowed to act (mol))/(total of diols used in the reaction (mol)) is in the range of 0.7 or more and 1.5 or less. When this value is less than 0.7, there is a risk that much of unreacted diols remains and the yield decreases; and when the value is more than 1.5, there is a risk that since much of the unreacted dicarboxylic acid derivative remains and the yield decreases.

The ester polymerization is preferably carried out under the condition of the reaction temperature of usually 350° C. or lower, and is desirably carried out by gradually raising the temperature with the progress of the reaction under the condition of more preferably 300° C. or lower. In the case where, as a result of the ester polymerization, by-products other than a polymer produced from a dicarboxylic acid derivative used can be removed by reduced pressure, in order to improve the reaction rate and the yield, the reaction is preferably carried out by simultaneously removing the by-products under a reduced pressure condition with the progress of the reaction. The reaction needs to be carried out for the reaction time until a target molecular weight is reached, and the reaction time is usually about 10 min to 12 hours.

The ester polymerization reaction can be carried out batchwise or continuously. The material and the structure of a reactor used are not especially limited, and the reactor suffices if having usual heating function and stirring function. The shape of the reactor may be not only of a tank type, but of an extruder type.

The ester polymerization reaction may be carried out in the presence of 1 to 200% by weight of an inactive organic solvent with respect to a polymer obtained. Here, inactive organic solvents include aromatic compounds such as diphenyl ether, halogenated diphenyl ether, benzophenone, diphenyl sulfone, polyphenyl ether, dichlorobenzene and methylnaphthalene, cycloalkanes such as tricyclo(5.2.10)decane, cyclooctane and cyclodecane, and chlorinated hydrocarbons such as dichloromethane (methylene chloride), chloroform, dichloroethane, trichloroethane, tetrachloroethane, pentachloroethane and chlorobenzene. Further, the ester polymerization reaction may be carried out under an inactive gas atmosphere as required. Here, inactive gases include, for example, helium, argon, carbon dioxide and nitrogen.

A polymer obtained by the above-mentioned three methods can be refined by a well-known method, and for example, can be refined by the reprecipitation method in a poor solvent such as methanol and water. By removing the residual solvent from a polymer obtained by the reprecipitation by heat drying under reduced pressure, the polycarbonate resin and the polyester resin according to the present invention can be manufactured. The drying temperature is preferably in the range of usually 100° C. to 350° C. The drying temperature less than 100° C. has a risk that the residual solvent cannot sufficiently be removed; and that exceeding 350° C. has a risk that the thermal decomposition of the polymer is caused and desired physical properties cannot be obtained.

In the polycarbonate resin and the polyester resin according to the present invention, additives may be added in the range of not impairing original purposes. Additives include substances including glass materials such as glass fibers, glass beads and glass powder, inorganic fillers of metal oxide microparticles of silicon oxide, titanium oxide, zirconium oxide, aluminum oxide and the like, phosphorus processing heat stabilizers, processing heat stabilizers such as hydroxylamines, antioxidants such as hindered phenols, light stabilizers such as hindered amines, ultraviolet absorbents such as benzotriazols, triazines, benzophenones and benzoates, plasticizers such as phosphates, phthalates, citrates and polyesters, release agents such as silicones, flame retardants such as phosphates and melamines, antistatic agents of fatty acid ester-based surfactants, organic coloring matters, and impact resistive improvers. These additives may be used singly or in combination thereof.

To the polycarbonate resin and the polyester resin according to the present invention, the above-mentioned additives can be mixed by a well-known method. The methods include, for example, a screw extruder, a roller type mill, a kneader mill, a mixer, a high pressure homogenizer, a wet media grinder (a bead mill, a ball mill, a disc mill) and an ultrasonic dispersion machine. The polycarbonate resin and the polyester resin thus obtained can be provided for manufacture of various types of molded articles and optical elements by a well-known processing method, for example, injection molding, blow molding, extrusion, press forming and calender molding.

When the polycarbonate resin and the polyester resin according to the present invention are molded by injection molding to fabricate an optical element, the polycarbonate resin and the polyester resin according to the present invention is preferably pelletized in advance by a pelletizer. The pellets are charged in an injection molding machine equipped with a kneading section including a melting cylinder and a screw, and heated, melted and kneaded in the kneading section, and injected to a molding metal mold of an arbitrary shape. By using a molding metal mold whose surface is a flat, concave or convex surface of an arbitrary shape subjected to mirror finishing, an optical element of an arbitrary shape can be manufactured.

When the polycarbonate resin and the polyester resin according to the present invention are molded by press molding to fabricate an optical element, the polycarbonate resin and the polyester resin according to the present invention is preferably powdered in advance by a grinder such as a mortar, a stamp mill and a ball mill. The powder is enclosed in a molding metal mold whose surface is a plat, concave or convex surface of an arbitrary shape subjected to mirror finishing; and the metal mold is heated to a temperature equal to or higher than the glass transition point of the resin to melt the resin, and a pressing pressure is imparted to manufacture an optical element of an arbitrary shape.

Example 1

Hereinafter, Examples according to the present invention will be described, but the scope of the present invention is not any more limited to these Examples.

Example 1-1

Synthesis of a Monomer (1a)

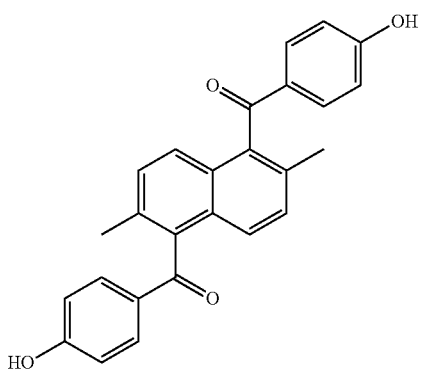

First, a di-halogeno-compound 6a shown below was synthesized.

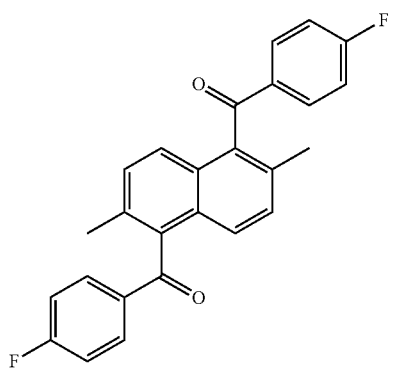

2,6-dimethylnaphthalene (30.0 g, 192 mmol), nitromethane (600 mL) and 4-fluorobenzoyl chloride (76.0 g, 481 mmol) were put in a 1-L recovery flask, and cooled to 0° C. Ground anhydrous aluminum chloride (63.9 g, 481 mmol) was gradually added thereto under stirring. The reaction liquid was stirred at room temperature for 1 hour, and thereafter was heated to 80° C. and allowed to react for 3 hours. The reaction mixture was cooled to room temperature, and poured in a cooled hydrochloric acid aqueous solution of 1.5 M concentration to terminate the reaction; and an oil layer was extracted, and dried with anhydrous magnesium sulfate; and thereafter, the solvent was distilled out by an evaporator. An obtained solid was recrystallized using a mixed solvent of methanol and acetone to obtain a di-halogeno-compound 6a (48.4 g, the yield was 63%).

Then, the di-halogeno-compound 6a (18.0 g, 45.0 mmol), dimethyl sulfoxide (100 mL) and potassium hydroxide (15.1 g, 270 mmol) were put in a 1-L recovery flask, and allowed to react at 180° C. for 20.5 hours. The reaction mixture was pored in a hydrochloric acid aqueous solution (400 mL) of 3 M concentration to precipitate a product. The obtained precipitate was washed with water and chloroform, thereafter injected with air for 2 hours to remove malodors, and dried under reduced pressure to obtain a monomer 1a (17.8 g, the quantitative yield (100%)).

Example 1-2

Synthesis of a Monomer (1b)

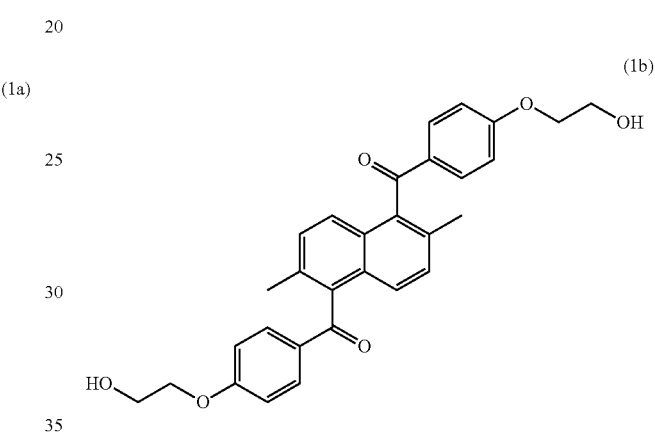

The monomer 1a (17.6 g, 44.4 mmol), N,N-dimethylformamide (100 mL), 2-chloroethanol (6.26 mL, 93.3 mmol) and cesium carbonate (43.4 g, 133 mmol) were put in a 500-mL recovery flask, and allowed to react at 100° C. for 14.5 hours. Ethyl acetate was added thereto; and an oil layer was extracted, dried with anhydrous magnesium sulfate; and thereafter, the solvent was removed under reduced pressure. The resultant was subjected to separation and refinement by silica gel chromatography using as a developing solvent a mixed solvent of chloroform and ethyl acetate (the mixing ratio was chloroform:ethyl acetate=1.5:2 to 0:1). The solvent was removed under reduced pressure to obtain a monomer 1b (6.59 g, the yield was 30%).

Example 1-3

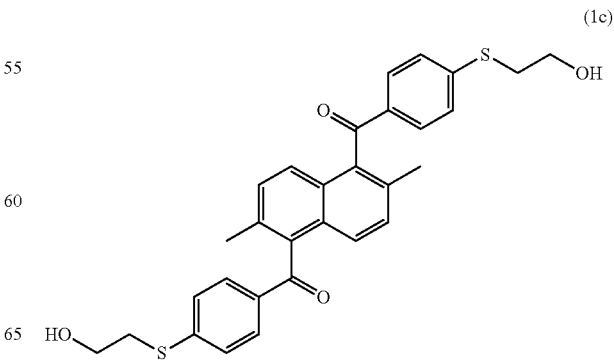

The di-halogeno-compound 6a (8.01 g, 20.0 mmol), dimethyl sulfoxide (100 mL) and 2-mercaptoethanol (70 mL, 1 mol) were put in a 500-mL recovery flask, and allowed to react at 100° C. for 12 hours. The reaction liquid was cooled to room temperature, made acidic with a hydrochloric aqueous solution (70 mL) of 3 M concentration, followed by addition of 500 mL of distilled water to deposit a product. The precipitate was recovered by filtration, and then washed with ethanol; and the obtained solid was dried under reduced pressure to obtain a monomer 1c (9.30 g, the yield was 90%).

Example 2-1

Synthesis of a Polycarbonate Polymer 1 of 1a

The monomer 1a (1.19 g, 3.00 mmol), sodium hydroxide (0.72 g, 18 mmol) and distilled water (30 mL) were put in a 100-mL recovery flask, and stirred to make a reaction solution. While the reaction solution was vigorously stirred under cooling at 5° C., a dichloromethane (30 mL) solution of bis(trichloromethyl)carbonate (0.594 g, 2.00 mmol) was added thereto, and trietylamine (14 µL, 0.100 mmol) was further added thereto, and the solution was continuously stirred for 15 min. Thereafter, the solution was continuously stirred at room temperature for 2 hours to complete the interfacial polycondensation reaction. The reaction mixture was pored in a hydrochloric acid aqueous solution of 3 M concentration, well stirred, and thereafter, a small amount of dichloromethane was added; and an oil layer was extracted. The oil layer was added to methanol under stirring to precipitate a polymerization product; and the obtained precipitate was filtered out, and dried under reduced pressure to obtain a polymer 1.

Example 2-2

Synthesis of a Polycarbonate Copolymer 2 of 1a (33%) and 12a (67%)

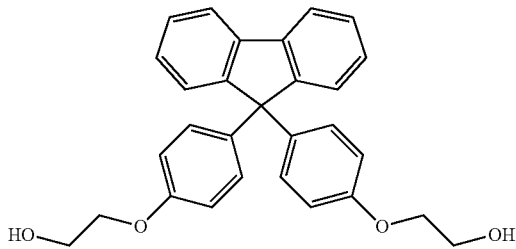

(12a)

The monomer 1a (500 mg, 1.26 mmol), a monomer 12a (product name: BPEF, made by Osaka Gas chemical Co., Ltd., 609 mg, 1.26 mmol), diphenyl carbonate (540 mg, 2.52 mmol) and 4-dimethylaminopyridine (0.30 mg, 2.5 µmol) were put in an argon atmosphere in a 20-mL Schlenk-type reaction tube, and heated and stirred at 80° C. for 30 min. Further, the reaction temperature was stepwise raised while the pressure in the reaction vessel was stepwise reduced (heating and stirring for 20 min at 400 hPa and 200° C.; then, for 20 min at 160 hPa and 220° C.; then, for 20 min at 40 hPa and 230° C.; and then, for 30 min at 1 hPa and 250° C.).

Thereafter, the reaction solution was cooled to room temperature; an obtained solid was dissolved in dichloromethane (20 mL); and the solution was added to methanol under stirring for reprecipitation. The obtained precipitate was dried under reduced pressure to obtain a polymer 2. The polymer 2 was dissolved in deuterated chloroform, and measured for proton NMR spectrum using a nuclear magnetic resonance spectrometer (product name: JEOL GTX 400, made by JEOL Ltd.), which confirmed that the ratio of the polymerized monomers was 1a:12a=1:2.

Example 2-3

Synthesis of a Polycarbonate Copolymer 3 of 1a (0.5%) and 12a (99.5%)

A polymer 3 was obtained under the same condition as in Example 2-2, except for altering the use amounts of the each monomer (the monomer 1a (5.9 g, 15.0 mmol) and the monomer 12a (19.7 g, 45.0 mmol)). The polymer 3 was dissolved in deuterated chloroform, and measured for proton NMR spectrum using a nuclear magnetic resonance spectrometer (product name: JEOL GTX 400, made by JEOL Ltd.), which confirmed that the ratio of the polymerized monomers was 1a:7a=0.5:99.5.

Example 2-4

Synthesis of a Polycarbonate Copolymer 4 of 1b (10%) and 12a (90%)

The monomer 1b (2.9 g, 6.0 mmol), the monomer 12a (23.7 g, 54.0 mmol), diphenyl carbonate (12.8 g, 60.0 mmol), di-tert-butyltin dilaurate (0.709 mL, 1.20 mmol), and triphenyl phosphite (0.631 mL, 2.40 mmol) as an antioxidant were put in an argon atmosphere in a 100-mL Schlenk-type reaction tube, and heated and stirred at 180° C. for 1.5 hours. Further, the reaction temperature was stepwise raised while the pressure in the reaction vessel was stepwise reduced (heating and stirring for 20 min at 400 hPa and 200° C.; then, for 20 min at 160 hPa and 220° C.; then, for 20 min at 40 hPa and 230° C.; and then, for 1 hour at 1 hPa and 250° C.).

Thereafter, the reaction solution was cooled to room temperature; an obtained solid was dissolved in N-dimethylformamide (70 mL); and the solution was added to methanol (450 mL) under stirring for reprecipitation. The obtained precipitate was dried under reduced pressure to obtain a polymer 4.

Example 2-5

Synthesis of a Polycarbonate Copolymer of 1b (25%) and 12a (75%)

A polymer 5 was obtained under the same condition as in Example 2-4, except for altering the use amounts of the each monomer (the monomer 1b (7.3 g, 15.0 mmol) and the monomer 12a (19.7 g, 45.0 mmol)).

Example 2-6

Synthesis of a Polycarbonate Polymer 6 of 1c

The monomer 1c (3.1 g, 6.0 mmol), diphenyl carbonate (1.3 g, 6.0 mmol), di-tert-butyltin dilaurate (0.071 mL, 0.12 mmol), and triphenyl phosphite (0.063 mL, 0.24 mmol) as an antioxidant were put in an argon atmosphere in a 100-mL Schlenk-type reaction tube, and heated and stirred at 180° C. for 1.5 hours. Further, the reaction temperature was stepwise raised while the pressure in the reaction vessel was stepwise reduced (heating and stirring for 20 min at 400 hPa and 200° C.; then, for 20 min at 160 hPa and 220° C.; then, for 20 min at 40 hPa and 230° C.; and then, for 1 hour at 1 hPa and 250° C.).

Thereafter, the reaction solution was cooled to room temperature; an obtained solid was dissolved in N-dimethylformamide (7 mL); and the solution was added to methanol (45 mL) under stirring for reprecipitation. The obtained precipitate was dried under reduced pressure to obtain a polymer 6.

Comparative Example 2-1

Synthesis of a Polycarbonate Polymer 7 of 12a

The monomer 7a (1.00 g, 2.28 mmol), diphenyl carbonate (489 mg, 2.28 mmol), 4-dimethylaminopyridine (2.8 mg, 2.3 μmol), and triphenyl phosphite (2.28 μL, 8.7 μmol) as an antioxidant were put in a 20-mL Schlenk-type reaction tube, and heated and stirred at 180° C. for 30 min. Further, the reaction temperature was stepwise raised while the pressure in the reaction vessel was stepwise reduced (heating and stirring for 20 min at 400 hPa and 200° C.; then, for 20 min at 160 hPa and 220° C.; then, for 20 min at 40 hPa and 230° C.; and then, for 30 min at 1 hPa and 250° C.).

Thereafter, the reaction solution was cooled to room temperature; an obtained solid was dissolved in dichloromethane (20 mL); and the solution was added to methanol (100 mL) under stirring for reprecipitation. The obtained precipitate was dried under reduced pressure to obtain a polymer 7.

Example 3-1

An example of fabrication of a circular disc molded article for an optical element The polymer 4 (0.30 g) was ground in an agate mortar, and thereafter put in a metal mold having a cylindrical shape of 15 mm inner diameter. Both surfaces of an open portion of the metal mold were enclosed with cylindrical metal molds of 15 mm diameter having a flat surface subjected to mirror surface treatment. The metal mold was heated at 200° C. for 10 min to melt the enclosed resin; and thereafter, a pressure of 50 MPa was impressed from both the surfaces of the metal mold. The metal mold was cooled to 100° C., and then the pressure was released, and a circular disc transparent molded article was obtained.

Analysis and Evaluation of Each Polymer

Analysis and evaluation methods of produced polymers are described. The analysis and evaluation items include molecular weight distribution measurement, and glass transition point and refractive index measurements, and hereinafter, measurement methods of each item are described in detail.

(1) Molecular Weight Distribution

A polymer was subjected to gel permission chromatography (GPC) using chloroform as a carrier liquid (0.085 mL/min). The analyzer used was a high performance liquid chromatograph (product name: Gulliver, made by JASCO Corp.) equipped with two types of polystyrene columns (product names: TSKgel G5000HXL and G4000HXL, made by Tosoh Corp.). By comparing the retention time of a polymer in the analyzer flow path with the retention times of standard polystyrenes whose molecular weights were already known, the number-average molecular weight (Mn) and the weight-average molecular weight (Mw) were approximately calculated.

(2) Glass Transition Point (Tg)

A polymer was measured in the range of ordinary temperature to 300° C. using a differential scanning calorimeter (DSC) (product name: DSC-60, made by Shimadzu Corp.) to determine the glass transition point (Tg).

(3) Refractive Index (nd) and Abbe Number (vd)

A polymer was dissolved in N-methyl-2-pyrrolidone; the solution was dropped on a glass substrate; thereafter, the temperature of the glass substrate was raised to 250° C. and held for 30 min; and the solvent was distilled out to form a film of 0.7 mm average thickness. The refractive index (nd) for the d spectrum line (wavelength: 587.56 nm) was measured at 27° C. using a Kalnew refractometer (product name: KPR-30, made by Shimadzu Device Corp.) to calculate the Abbe number (vd) of the polymer.

The results obtained for the each polymer are shown in Table 1 shown below.

TABLE 1

|  | First Polymer | monomer | Ratio | Second monomer | Ratio | Mn | Mw/Mn | Tg (° C.) | nd | vd |
|---|---|---|---|---|---|---|---|---|---|---|
| Example 2-1 | 1 | 1a | 100% | None |  | 6900 | 1.9 | 265 | 1.682 | 15.19 |
| Example 2-2 | 2 | 1a | 33% | 12a | 67% | 1300 | 2.0 | 118 | 1.651 | 19.44 |
| Example 2-3 | 3 | 1a | 0.5% | 12a | 99.5% | 1400 | 2.3 | 130 | 1.635 | 24.82 |
| Example 2-4 | 4 | 1b | 10% | 12a | 90% | 3500 | 2.4 | 129 | 1.638 | 22.68 |
| Example 2-5 | 5 | 1b | 25% | 12a | 75% | 2500 | 2.1 | 148 | 1.657 | 21.20 |
| Example 2-6 | 6 | 1c | 100% | None |  | 8800 | 2.3 | 124 | 1.687 | 15.55 |
| Comparative Example 2-1 | 7 | 12a | 100% | None |  | 6400 | 3.7 | 150 | 1.639 | 22.89 |

As is clear from the results described in Table 1, the polymers of Examples 2-1, 2-2, 2-5 and 2-6 exhibited a higher refractive index than the homopolymer of a well-known monomer of Comparative Example 2-1. The polymers of Examples 2-1, 2-2, 2-4, 2-5 and 2-6 exhibited a lower Abbe number than the homopolymer of a well-known monomer of Comparative Example 2-1. Further, the polymers of Examples 2-2, 2-3, 2-4, 2-5 and 2-6 had a lower glass transition point, and could be melt processed at a lower temperature than the homopolymer of a well-known monomer of Comparative Example 2-1.

From the above, it is clear that the resin according to the present invention was improved in at least one characteristic among properties of high refractive index, low Abbe number and low glass transition temperature as compared with the homopolymer of a well-known monomer. From this fact, it can be said that the use of the diol according to the present invention can make the resin according to the present invention adjustable to a desired refractive index, Abbe number and glass transition point corresponding to various types of optical systems, and the diol is useful as a raw material of high-refractive index thermoplastic resins for optics.

Second Embodiment

The diol according to the present invention is characterized by including a compound represented by the following general formula (3):

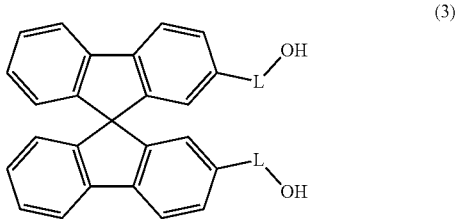

(3)

In the general formula (3), L denotes one of an oxyalkylene group having 2 or more and 12 or less, preferably 2 or more and 6 or less carbon atoms and a poly(oxyethylene) group having 2 or more and 12 or less, preferably 2 or more and 4 or less carbon atoms. In the case where the number of carbon contained in L in the structure of a diol represented by the general formula (3) is less than 2, the glass transition point of a polycarbonate resin and a polyester resin obtained by polymerizing the diol becomes high and melt molding by heating becomes difficult. With the number of carbon exceeding 12, a molded article of a polycarbonate resin and a polyester resin obtained by polymerizing the diol hardly provide a sufficient shape stability to heat.

Then, a method for manufacturing the diol according to the present invention is described.

A diol represented by the general formula (3) can be manufactured by allowing a halogenated alcohol represented by the general formula (14) shown below to act on 2,2'-dihydroxy-9,9'-spirobifluorene represented by the formula (13a) shown below in the presence of cesium carbonate or the like.

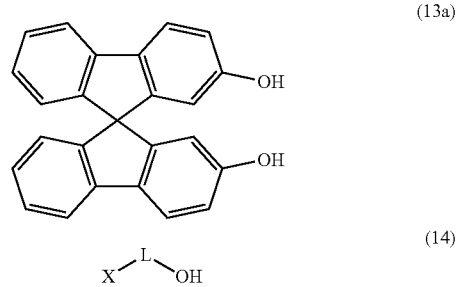

(13a)

(14)

$$X \diagdown L \diagdown OH$$

wherein X denotes one of fluorine, chlorine bromine and iodine atoms; and L denotes one of an oxyalkylene group having 2 or more and 12 or less carbon atoms and a poly (oxyethylene) group having 2 or more and 12 or less carbon atoms.

Among these, 2,2'-dihydroxy-9,9'-spirobifluorene can be synthesized by a method described in Helv. Chim. Acta, vol. 62, pp. 2285-2302 (1979), or other methods.

The stoichiometric ratio of a halogenated alcohol represented by the general formula (14), allowed to act on 2,2'-dihydroxy-9,9'-spirobifluorene, is preferably such that (halogenated alcohol allowed to act (mol))/(2,2'-dihydroxy-9,9'-spirobifluorene (mol)) is 2 or more and 100 or less. When this value is less than 2, there is a risk that by-products are produced and the yield of a diol represented by the general formula (3) decreases; and when the value is more than 100, there is a risk that the use amount of a halogenated alcohol represented by the general formula (14) becomes much and the cost becomes high in production.

The reaction conditions are not especially limited, but the reaction solvent is generally a polar solvent such as N,N-dimethylformamide and dimethyl sulfoxide; the reaction temperature is 100° C. to 150° C.; and the reaction time needs to be 12 hours to 48 hours. An obtained product can easily be refined by a method such as recrystallization and chromatography.

The polycarbonate resin and the polyester resin according to the present invention obtained by polymerizing a diol represented by the general formula (3) according to the present invention are resins having a relatively high refractive index, but simultaneously having a low birefringence. Polymers having aromatic rings in the molecule generally have high molecular orientation, and are consequently apt to be resin materials having high birefringence. However, since the spirobifluorene skeleton in a diol represented by the general formula (3) has a highly symmetrical structure in which two fluorene ring planes are perpendicular, it is conceivable that the intrinsic birefringence per unit skeleton is small and the birefringence of the resin is consequently reduced.

Further, an oxyalkylene group having 2 or more and 12 or less carbon atoms and a poly(oxyethylene) group having 2 or more and 12 or less carbon atoms denoted as L in the general formula (3) have a function of reducing the glass transition point of a polymer obtained by polymerizing a diol represented by the general formula (3). The reduction of the glass transition point can improve the processability during melting and simultaneously decrease melt viscoelasticity, and can reduce the stress birefringence on processing. The combination of these characteristics presumably results in the condition that the polycarbonate resin and the polyester resin according to the present invention have low birefringence.

The polycarbonate resin and the polyester resin according to the present invention are synthesized by using a diol represented by the general formula (3) as a polymerization component, and are characterized by containing in the polymers a repeating unit represented by the general formula (4):

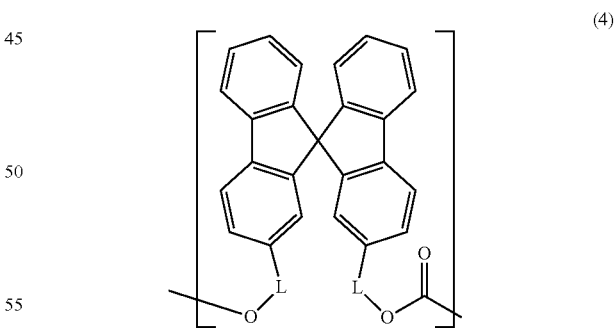

(4)

wherein L denotes one of an oxyalkylene group having 2 or more and 12 or less carbon atoms and a poly(oxyethylene) group having 2 or more and 12 or less carbon atoms.

Here, the molar fraction of the repeating unit represented by general formula (4) is preferably 10% or more, and more preferably 25% or more. Here, the molar fraction of a repeating unit refers to a percentage value obtained by dividing the number of the repeating unit represented by general formula (4) by the sum of the numbers of all repeating units in a polymer. A larger molar fraction of a repeating unit represented by general formula (4) results in the condition that the high refractive index which a diol analog of the general formula (3) has is more strongly reflected on the polymer.

Other copolymerization components in a polymer are not especially limited as long as meeting desired characteristics, but copolymerization components represented by the general formulae (12) and (13) shown below can be more suitably included.

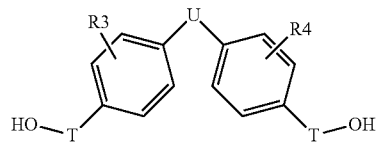

(12)

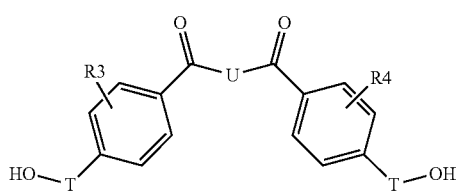

(13)

wherein in the general formulae (12) and (13), T denotes one of an oxyalkylene group having 2 or more and 12 or less carbon atoms, a poly(oxyethylene) group having 2 or more and 12 or less carbon atoms, and a single bond; R3 and R4 each denote one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.

These copolymerization components may be used singly or plurally.

In the case of using a diol represented by the general formula (12) or (13) as a copolymerization component, a synthesized polymer contains at least one type of repeating units selected from repeating units represented by the following general formulae (5) and (6):

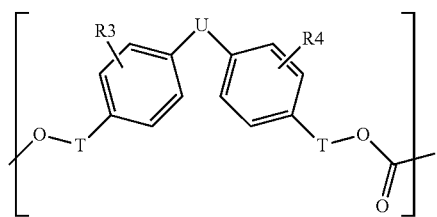

(5)

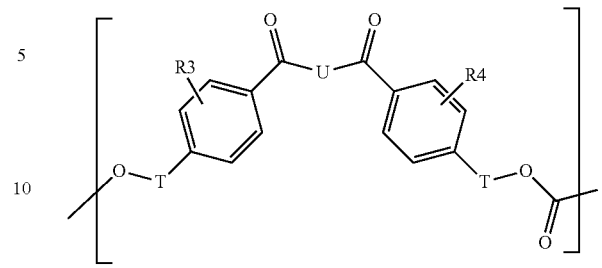

(6)

wherein in the general formulae (5) and (6), T denotes one of an oxyalkylene group having 2 or more and 12 or less carbon atoms, a poly(oxyethylene) group having 2 or more and 12 or less carbon atoms, and a single bond; R3 and R4 each denote one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.

In this case, the thermal stability and optical characteristics of a diol analog of the general formula (12) or (13) are reflected on the polymer depending on the copolymerization ratio.

A diol represented by the general formula (13) includes a diol of the general formula (1) described in the first embodiment. Therefore, the repeating unit represented by the general formula (6) includes the repeating unit represented by the general formula (2), and the same may be said of the polycarbonate resin including the repeating unit.

In the case where the polycarbonate resin and the polyester resin according to the present invention include repeating units represented by the general formulae (5) and (6), the molar fraction of the polycarbonate resin and the polyester resin is preferably 90% or less, and more preferably 75% or less.

In the case where the polycarbonate resin and the polyester resin according to the present invention include an optional repeating unit other than the residues of diols represented by the general formulae (4), (5) and (6), the molar fraction of the repeating unit other than the general formulae (4), (5) and (6) is preferably 10% or less. Here, the molar fraction of the repeating unit refers to a percentage value obtained by dividing the total number of the repeating units other than the general formulae (4), (5) and (6) by the sum of the numbers of all the repeating units in the polymer. If the molar fraction of the repeating units other than the general formulae (4), (5) and (6) exceeds 10%, there arises a risk that desired physical properties such as thermal stability, high refractive index and low birefringence cannot be provided.

The polycarbonate resin and the polyester resin according to the present invention can be efficiently manufactured by three methods described in the first embodiment.

Example 4

Hereinafter, Examples according to the present invention will be described, but the scope of the present invention is not any more limited to these Examples.

Example 4-1

Synthesis of a Monomer (3a)

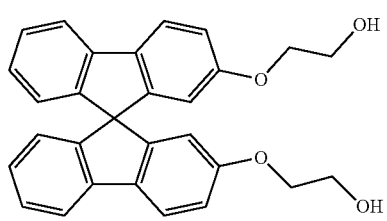

(3a)

First, 2,2'-dihydroxy-9,9'-spirobifluorene (13a):

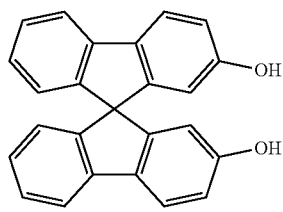

(13a)

as a precursor of the monomer (3a) was synthesized.

Aluminum chloride (127 g, 0.948 mol) and nitromethane (250 mL) were put in a 1-L four-necked flask. Acetyl chloride (67.3 mL, 0.948 mol) was added to the solution, and the solution was held at 0° C. To the solution, a solution in which 9,9'-spirobifluorene (15):

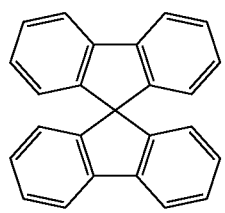

(15)

(100 g, 0.316 mol) was dissolved in dried dichloromethane (300 mL) was dropwise added over 1 hour. The solution was stirred at 0° C. for 1 hour, and warmed to room temperature and stirred for 2 hours. The solution after the reaction was poured in a hydrochloric acid aqueous solution (1M concentration) with ice to decompose unreacted aluminum chloride; and thereafter, an organic layer was washed with a sodium hydrogencarbonate-saturated aqueous solution and a sodium chloride-saturated aqueous solution. The organic layer was dried with anhydrous magnesium sulfate, and thereafter the solvent was removed under reduced pressure to obtain a solid material. The solid material was dissolved in dichloromethane, and thereafter poured in n-hexane for reprecipitation to obtain 2,2'-diacetyl-9,9'-spirobifluorene (16):

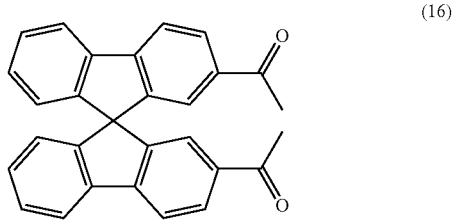 [SMILES: CC(=O)c1ccc2c(c1)C1(c3ccccc3-2)c2ccccc2-c2ccc(C(C)=O)cc21]

(16)

(95.4 g, the yield was 76%).

Next, the 2,2'-diacetyl-9,9'-spirobifluorene (16) (10.0 g, 25 mmol) and meta-chloroperbenzoic acid (40%-hydrous) (21.6 g, 75 mmol) were put in a 500-mL recovery flask, and thereafter heated under reflux for 12 hours.

The solution was cooled to room temperature followed by addition of a sodium sulfite-saturated aqueous solution and stirred; and an organic layer was washed with a sodium hydrogencarbonate-saturated aqueous solution and a sodium chloride-saturated aqueous solution. The organic layer was dried with anhydrous magnesium sulfate, and thereafter the solvent was removed under reduced pressure. The separation and refinement was carried out by silica gel chromatography using as a developing solvent a mixed solvent of ethyl acetate, n-hexane and dichloromethane (the mixing ratio was ethyl acetate:n-hexane:dichloromethane=1:4:2). The resultant was dried under reduced pressure to remove the solvent to obtain 2,2'-diacetoxy-9,9'-spirobifluorene (17):

(17)

(9.45 g, the yield was 87%).

The 2,2'-diacetoxy-9,9'-spirobifluorene (17) (6.35 g, 14.7 mmol) and methanol (20 mL) were put in a 100-mL recovery flask. To the solution, an aqueous solution (10 mL) in which sodium hydroxide (1.25 g, 31.3 mmol) was dissolved was added, and stirred at room temperature for 30 min.

A dilute hydrochloric acid (3 M concentration) was added thereto to acidify the solution, and thereafter an organic layer was extracted using diethyl ether. The organic layer was washed with a sodium chloride-saturated aqueous solution, and dried with anhydrous magnesium sulfate; and the solvent was removed under reduced pressure. The separation and refinement was carried out by silica gel chromatography using as a developing solvent a mixed solvent of ethyl acetate and n-hexane (the mixing ratio was ethyl acetate:n-hexane=1:4). The resultant was dried under reduced pressure to remove the solvent to obtain 2,2'-dihydroxy-9,9'-spirobifluorene (13a) (5.05 g, the yield was 99%).

The 2,2'-dihydroxy-9,9'-spirobifluorene (13a) (1.50 g, 4.31 mmol) synthesized by the above method, N,N-dimethylformamide (10 mL), 2-chloroethanol (0.604 mL, 9.00 mmol) and cesium carbonate (2.93 g, 9.00 mmol) were put in a 100-mL two-necked recovery flask, and stirred in an argon atmosphere at 110° C. for 12 hours.

After the completion of the reaction, the resultant was poured in water to cause N,N-dimethylformamide and cesium carbonate to be dissolved in water; and a remaining solid material was filtered. The solid material was dissolved in dichloromethane, and the solution was dried with anhydrous magnesium sulfate, and thereafter, the solvent was removed under reduced pressure. The separation and refinement was carried out by silica gel chromatography using as a developing solvent a mixed solvent of ethyl acetate and n-hexane (the mixing ratio was ethyl acetate:n-hexane=1:2 to 3:2). The resultant was dried under reduced pressure to remove the solvent to obtain a monomer 3a (933 mg, the yield was 50%).

Example 4-2

Synthesis of a Monomer (3b)

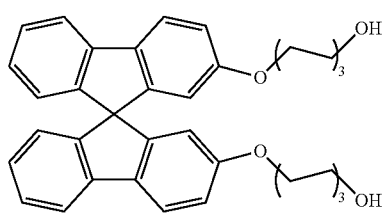

(3b)

The reaction was carried out under the same condition as in Example 4-1, except for using 2-bromohexanol (1.22 mL, 9.00 mmol) in place of 2-chloroethanol to consequently obtain a monomer 3b (1.30 g, the yield was 55%).

Example 4-3

Synthesis of a Monomer (3c)

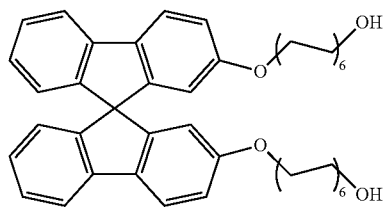

(3c)

The reaction was carried out under the same condition as in Example 4-1, except for using 12-bromododecanol (1.83 g, 6.90 mmol) in place of 2-chloroethanol to consequently obtain a monomer 3c (1.02 g, the yield was 33%).

Example 4-4

Synthesis of a Monomer (3d)

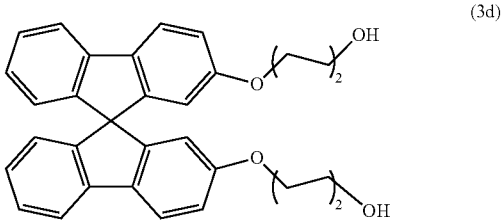

(3d)

The reaction was carried out under the same condition as in Example 4-1, except for using 2-(2-chloroethoxy)ethanol (0.949 mL, 9.00 mmol) in place of 2-chloroethanol; and after the reaction, the separation and refinement was carried out by silica gel chromatography using ethanol as a developing solvent. The resultant was dried under reduced pressure to remove the solvent to consequently obtain a monomer 3d (2.04 g, the yield was 86%).

Example 4-5

Synthesis of a Monomer 3(e)

Formula 33

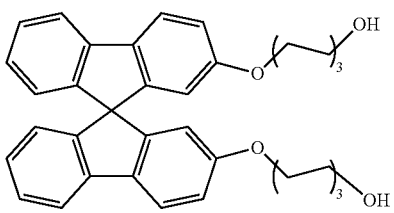

(3e)

The 2,2'-dihydroxy-9,9'-spirobifluorene 5 (4.00 g, 11.5 mmol), N,N-dimethylformamide (40 mL), 2-{2-(2-chloroethoxy)ethoxy}ethanol (3.64 mL, 25.0 mmol) and cesium carbonate (8.14 g, 25.0 mmol) were put in a 100-mL two-necked recovery flask, and stirred in an argon atmosphere at 110° C. for 12 hours.

After the completion of the reaction, the resultant was poured in water to cause N,N-dimethylformamide and cesium carbonate to be dissolved in water; and a remaining solid material was filtered. The solid material was dissolved in dichloromethane, and the solution was dried with anhydrous magnesium sulfate, and thereafter, the solvent was removed under reduced pressure. The separation and refinement was carried out by silica gel chromatography using as a developing solvent a mixed solvent of ethyl acetate and n-hexane (the mixing ratio was ethyl acetate:methanol=1:9:1). The resultant was dried under reduced pressure to remove the solvent to obtain a monomer 3e (6.23 g, the yield was 86%).

Example 5-1

Synthesis of a Polycarbonate Polymer (11) of 3a

The monomer 3a (800 mg, 1.83 mmol), diphenyl carbonate (393 mg, 1.83 mmol) and 4-dimethylaminopyridine (2.24 mg, 18.3 µmol) were put in an argon atmosphere in a 20-mL Schlenk-type reaction tube, and heated and stirred at 180° C. for 30 min. Further, the reaction temperature was stepwise raised while the pressure in the reaction vessel was stepwise reduced (heating and stirring for 20 min at 400 hPa and 200° C.; then, for 20 min at 160 hPa and 220° C.; then, for 20 min at 40 hPa and 230° C.; and then, for 30 min at 1 hPa and 250° C.).

Thereafter, the reaction solution was cooled to room temperature; an obtained solid was dissolved in dichloromethane (20 mL); and the solution was added to methanol (100 mL) under stirring for reprecipitation. The obtained precipitate was dried under reduced pressure to obtain a polymer (11) (745 mg, the yield was 88%).

Example 5-2

Synthesis of a Polycarbonate Copolymer (12) of 3a (90%) and 12a (10%)

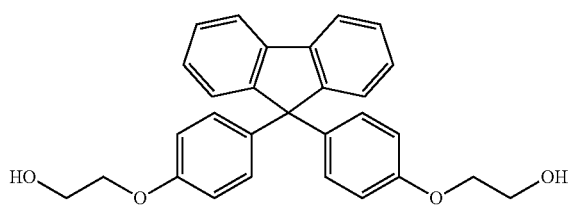

(12a)

The monomer 3a (1.80 g, 4.12 mmol), the monomer 12a (product name: BPEF, made by Osaka Gas Chemical Co., Ltd.) (201 mg, 0.458 mmol), diphenyl carbonate (981 mg, 4.58 mmol) and 4-dimethylaminopyridine (5.6 mg, 45.8 µmol) were put in an argon atmosphere in a 20-mL Schlenk-type reaction tube. Then, the reaction and the aftertreatment were carried out under the same conditions in Example 5-1 to obtain a polymer (12) (1.59 g, the yield was 75%).

Example 5-3

Synthesis of a Polycarbonate Copolymer (13) of 3a (75%) and 12a (25%)

The monomer 3a (1.50 g, 3.44 mmol), the monomer 12a (502 mg, 1.15 mmol), diphenyl carbonate (981 mg, 4.58 mmol) and 4-dimethylaminopyridine (5.6 mg, 45.8 µmol) were put in an argon atmosphere in a 20-mL Schlenk-type reaction tube. Then, the reaction and the aftertreatment were carried out under the same conditions in Example 5-1 to obtain a polymer (13) (1.63 g, the yield was 77%).

Example 5-4

Synthesis of a Polycarbonate Copolymer (14) of 3a (50%) and 12a (50%)

The monomer 3a (1.00 g, 2.29 mmol), the monomer 12a (1.01 mg, 2.29 mmol), diphenyl carbonate (981 mg, 4.58 mmol) and 4-dimethylaminopyridine (5.6 mg, 45.8 mmol) were put in an argon atmosphere in a 20-mL Schlenk-type reaction tube. Then, the reaction and the aftertreatment were carried out under the same conditions in Example 5-1 to obtain a polymer (14) (1.68 g, the yield was 79%).

Example 5-5

Synthesis of a Polycarbonate Copolymer (15) of 3a (25%) and 12a (75%)

The monomer 3a (500 mg, 1.15 mmol), the monomer 12a (1.51 g, 3.44 mmol), diphenyl carbonate (981 mg, 4.58 mmol) and 4-dimethylaminopyridine (5.6 mg, 45.8 mol) were put in an argon atmosphere in a 20-mL Schlenk-type reaction tube. Then, the reaction and the aftertreatment were carried out under the same conditions in Example 5-1 to obtain a polymer (15) (1.83 g, the yield was 86%).

Example 5-6

Synthesis of a Polycarbonate Copolymer (16) of 3a (10%) and 12a (90%)

The monomer 3a (200 mg, 0.458 mmol), the monomer 12a (1.81 g, 4.12 mmol), diphenyl carbonate (981 mg, 4.58 mmol) and 4-dimethylaminopyridine (5.6 mg, 45.8 µmol) were put in an argon atmosphere in a 20-mL Schlenk-type reaction tube. Then, the reaction and the aftertreatment were carried out under the same conditions in Example 5-1 to obtain a polymer (16) (1.81 g, the yield was 85%).

Example 5-7

Synthesis of a Polycarbonate Polymer (17) of 3b

The monomer 3b (427 mg, 0.779 mmol), diphenyl carbonate (162 mg, 0.779 mmol) and 4-dimethylaminopyridine (0.951 mg, 7.8 mol) were put in an argon atmosphere in a 20-mL Schlenk-type reaction tube. Then, the reaction and the aftertreatment were carried out under the same conditions in Example 5-1 to obtain a polymer (17) (412 mg, the yield was 92%).

Example 5-8

Synthesis of a Polycarbonate Polymer (18) of 3c

The monomer 3c (668 mg, 0.931 mmol), diphenyl carbonate (199 mg, 0.931 mmol) and 4-dimethylaminopyridine (1.13 mg, 9.3 µmol) were put in an argon atmosphere in a 20-mL Schlenk-type reaction tube. Then, the reaction and the aftertreatment were carried out under the same conditions in Example 5-1 to obtain a polymer (18) (567 mg, the yield was 82%).

Example 5-9

Synthesis of a Polycarbonate Polymer (19) of 3d

The monomer 3d (1.77 mg, 3.38 mmol), diphenyl carbonate (724 mg, 3.38 mmol), 4-dimethylaminopyridine (4.13 mg, 33.8 µmol), and triphenyl phosphite (3.38 µL, 12.9 µmol) as an antioxidant were put in an argon atmosphere in a 20-mL Schlenk-type reaction tube. Then, the reaction and the aftertreatment were carried out under the same conditions in Example 5-1 to obtain a polymer (19) (1.46 g, the yield was 78%).

Example 5-10

Synthesis of a Polycarbonate Polymer (20) of 3e

The monomer 3e (1.14 g, 1.82 mmol), diphenyl carbonate (390 mg, 1.82 mmol) and 4-dimethylaminopyridine (2.22 mg, 18.2 μmol) were put in an argon atmosphere in a 20-mL Schlenk-type reaction tube. Then, the reaction and the after-treatment were carried out under the same conditions in Example 5-1 to obtain a polymer (20) (1.10 g, the yield was 95%).

Comparative Example 5-1

Synthesis of a Polycarbonate Polymer (21) of 12a

The monomer 12a (1.00 g, 2.28 mmol), diphenyl carbonate (489 mg, 2.28 mmol), 4-dimethylaminopyridine (2.8 mg, 22.8 μmol), and triphenyl phosphite (2.28 μL, 8.7 μmol) as an antioxidant were put in an argon atmosphere in a 20-mL Schlenk-type reaction tube. Then, the reaction and the after-treatment were carried out under the same conditions in Example 5-1 to obtain a polymer (21) (932 mg, the yield was 88%).

Example 6-1

An example of fabrication of a circular disc molded article for an optical element The polymer 11 (0.30 g) was ground in an agate mortar, and thereafter put in a metal mold having a cylindrical shape of 15 mm inner diameter. Both surfaces of an open portion of the metal mold were enclosed with cylindrical metal molds of 15 mm diameter having a flat surface subjected to mirror surface treatment. The metal mold was heated at 200° C. for 10 min to melt the enclosed resin; and thereafter, a pressure of 50 MPa was impressed from both the surfaces of the metal mold. The metal mold was cooled to 100° C., and then the pressure was released, and a circular disc transparent molded article was obtained.

Analysis and Evaluation of Each Polymer

Each polymer of the Examples was analyzed and evaluated by the same method of the analysis and evaluation described in the first embodiment. The results obtained for the each polymer are shown in Table 2 shown below.

Relationships between composition ratios and optical characteristics of the copolymers of the monomers 3a and 12a, determined from the results in Table 2, are shown in Table 3 shown below and FIG. 1.

TABLE 3

| Polymer | 3a | nd | vd |
|---|---|---|---|
| 11 | 100 | 1.661 | 18.52 |
| 12 | 90 | 1.664 | 18.70 |
| 13 | 75 | 1.661 | 19.38 |
| 14 | 50 | 1.654 | 20.25 |
| 15 | 25 | 1.648 | 21.66 |
| 16 | 10 | 1.640 | 22.13 |
| 21 | 0 | 1.639 | 22.89 |

Figure 2:
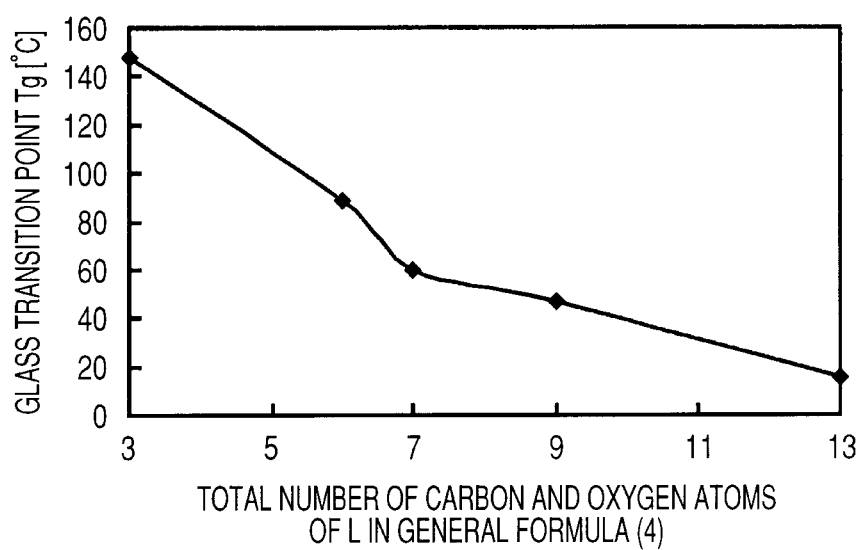
FIG. 2 is a graph illustrating a relationship between the total number of carbon and oxygen atoms of L in the general formula (4) and the glass transition point.

The relationship between the total number of carbon and oxygen atoms in L in the general formula (4) and the glass transition point, determined from the results in Table 2, are shown in Table 4 shown below and FIG. 2.

TABLE 4

| Polymer | Monomer | Total number of carbon atom + oxygen atom of L | Tg (° C.) | nd | vd |
|---|---|---|---|---|---|
| 11 | 3a | 3 | 148 | 1.661 | 18.52 |
| 19 | 3d | 6 | 89 | 1.644 | 20.06 |
| 17 | 3b | 7 | 60 | 1.652 | 17.30 |
| 20 | 3e | 9 | 47 | 1.629 | 21.18 |
| 18 | 3c | 13 | 16 | 1.653 | 17.36 |

As is clear from the results described in Table 2 and FIG. 1, the polymers of Examples 5-1 to 5-9 exhibited a higher refractive index than the homopolymer of a well-known monomer of Comparative Example 5-1. Any of the polymers of Examples 5-1 to 5-10 exhibited a low Abbe number than the homopolymer of a well-known monomer of Comparative Example 5-1.

Any polymer of the Examples had a glass transition point of 156° C. or lower, and could easily be processed by heating. As shown in FIG. 2, resins having various glass transition temperatures could be manufactured corresponding to lengths of molecular chains of an oxyalkylene group and a poly(oxyethylene) group denoted as L in the repeating unit structure represented by the general formula (4). Above all, since the polymers of Examples 5-1, and 5-5 to 5-10 had a lower glass transition point than the homopolymer of a well-known monomer of Comparative Example 5-1, these polymers could be molded at lower temperatures.

TABLE 2

| | Polymer | First monomer | Ratio | Second monomer | Ratio | Mn | Mw/Mn | Tg(° C.) | nd | vd |
|---|---|---|---|---|---|---|---|---|---|---|
| Example 5-1 | 11 | 3a | 100% | None | | 12700 | 2.5 | 148 | 1.661 | 18.52 |
| Example 5-2 | 12 | 3a | 90% | 12a | 10% | 1800 | 5.1 | 153 | 1.664 | 18.70 |
| Example 5-3 | 13 | 3a | 75% | 12a | 25% | 2300 | 5.5 | 156 | 1.661 | 19.38 |
| Example 5-4 | 14 | 3a | 50% | 12a | 50% | 3000 | 8.2 | 154 | 1.654 | 20.25 |
| Example 5-5 | 15 | 3a | 25% | 12a | 75% | 3500 | 5.4 | 149 | 1.648 | 21.66 |
| Example 5-6 | 16 | 3a | 10% | 12a | 90% | 10100 | 3.0 | 140 | 1.640 | 22.13 |
| Example 5-7 | 17 | 3b | 100% | None | | 6100 | 2.1 | 60 | 1.652 | 17.30 |
| Example 5-8 | 18 | 3c | 100% | None | | 3900 | 3.6 | 16 | 1.653 | 17.36 |
| Example 5-9 | 19 | 3d | 100% | None | | 5500 | 2.2 | 89 | 1.644 | 20.06 |
| Example 5-10 | 20 | 3e | 100% | None | | 15100 | 2.1 | 47 | 1.629 | 21.18 |
| Comparative Example 5-1 | 21 | 12a | 100% | None | | 6400 | 3.7 | 150 | 1.639 | 22.89 |

From the above, it is clear that the resin according to the present invention is improved in at least one characteristic among properties of high refractive index, low Abbe number and low glass transition point as compared with the homopolymer of a well-known monomer. From this fact, it can be said that the use of the diol according to the present invention can make the resin according to the present invention adjustable to a desired refractive index, Abbe number and glass transition point according to various types of optical systems, and the diol are especially useful as a raw material of a high-refractive index thermoplastic resin for optics.

INDUSTRIAL APPLICABILITY

Since from the diol according to the present invention, a resin material having high processability and a high refractive index can be manufactured, the diol can be utilized for molded articles, and lenses for cameras and the like, lenses for optical disks, fθ lenses, optical elements of image display media, optical films and optical elements such as prisms, which are formed of a polycarbonate resin or a polyester resin which is a polymer of the diol.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A polycarbonate resin comprising in a polymer thereof a repeating unit represented by general formula (2):

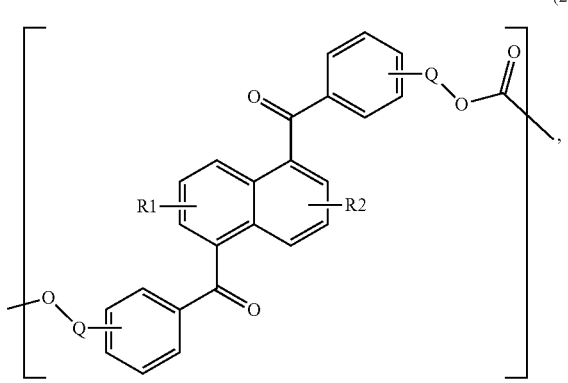

wherein R1 and R2 each independently denotes one of a hydrogen atom and an alkyl group having 1 or more and 6 or less carbon atoms; Q denotes one of an oxyethylene group, a thioethylene group and a single bond.

2. The polycarbonate resin according to claim 1, wherein the polymer has a molar fraction of the repeating unit represented by the general formula (2) of 10% or more.

3. The polycarbonate resin according to claim 2, further comprising a repeating unit represented by general formula (5):

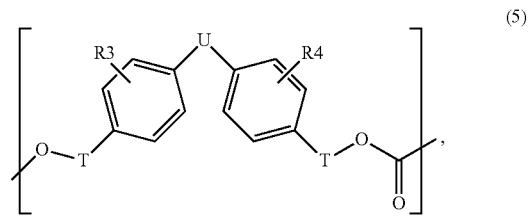

wherein T denotes one of an oxyalkylene group having 2 or more and 12 or less carbon atoms, a poly(oxyethylene) group having 2 or more and 12 or less carbon atoms, and a single bond; R3 and R4 each denotes one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.

4. A polycarbonate resin comprising a repeating unit represented by general formula (2) and a repeating unit represented by general formula (6), further comprising a repeating unit represented by general formula (5):

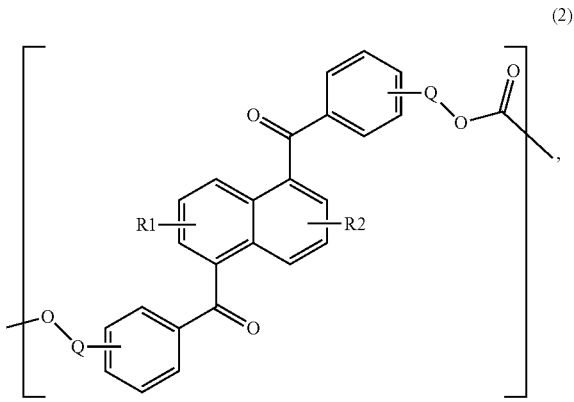

wherein R1 and R2 each independently denotes one of a hydrogen atom and an alkyl group having 1 or more and 6 or less carbon atoms; Q denotes one of an oxyethylene group, a thioethylene group and a single bond;

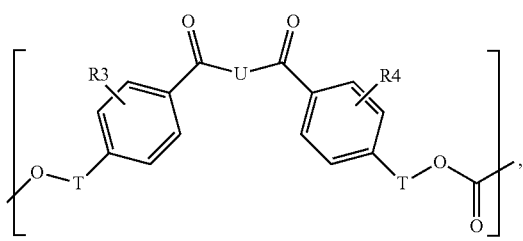

wherein T denotes one of an oxyalkylene group having 2 or more and 12 or less carbon atoms, a poly(oxyethylene) group having 2 or more and 12 or less carbon atoms, and a single bond; R3 and R4 each denotes one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit; and

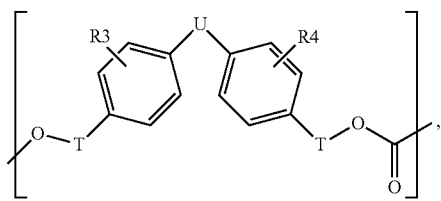
(5)

wherein T denotes one of an oxyalkylene group having 2 or more and 12 or less carbon atoms, a poly(oxyethylene) group having 2 or more and 12 or less carbon atoms, and a single bond; R3 and R4 each denotes one of a hydrogen atom, an alkyl group having 1 or more and 6 or less carbon atoms, an alkoxy group having 1 or more and 6 or less carbon atoms, and an aryl group having 6 or more and 12 or less carbon atoms, and may be the same or different from each other; U denotes one of an alkylene group having 1 or more and 13 or less carbon atoms, an alkylidene group having 2 or more and 13 or less carbon atoms, a cycloalkylene group having 5 or more and 13 or less carbon atoms, a cycloalkylidene group having 5 or more and 13 or less carbon atoms, an arylene group having 6 or more and 13 or less carbon atoms, fluorenidene, —O—, —S—, —SO$_2$—, —CO—, and a single bond; and R3, R4, T and U may be different for every structural unit.

5. A molded article comprising a polycarbonate resin according to claim 1.

6. An optical element comprising a polycarbonate resin according to claim 1.

7. A molded article comprising a polycarbonate resin according to claim 2.

8. An optical element comprising a polycarbonate resin according to claim 2.

* * * * *